United States Patent [19]
Lanier et al.

[11] 3,938,958
[45] Feb. 17, 1976

[54] FLUID DISPENSING DEVICE
[75] Inventors: Terry O. Lanier, Northboro; Eugene F. Martha, North Attleboro, both of Mass.
[73] Assignee: Corning Glass Works, Corning, N.Y.
[22] Filed: Mar. 24, 1975
[21] Appl. No.: 561,267

[52] U.S. Cl. ............... 23/259; 23/253 R; 141/83; 141/102; 141/130; 195/127; 73/425.4 R
[51] Int. Cl.² ..................... G01N 1/14; G01N 31/20
[58] Field of Search ........... 23/253 R, 259; 141/130, 141/83, 100, 102; 195/127; 73/425.4 R

[56] References Cited
UNITED STATES PATENTS
| | | | |
|---|---|---|---|
| 3,490,876 | 1/1970 | Auphan | 23/253 R |
| 3,776,184 | 12/1973 | Harrison | 23/253 R |
| 3,807,959 | 4/1974 | Russell et al. | 23/253 R |
| 3,859,051 | 1/1975 | Nelson | 23/253 R |

*Primary Examiner*—R. E. Serwin
*Attorney, Agent, or Firm*—Walter S. Zebrowski; Clarence R. Patty, Jr.

[57] ABSTRACT

A fluid dispensing device suitable for accepting one or more discrete quantities of test fluids and thereafter dispensing predetermined quantities of such fluid or fluids to a test vehicle. The device operates on a disposable applicator card containing one or more compressible tubes which are filled with such fluid or fluids from a sample tray by peristaltic-like action. The dispensing device permits proper alignment with respect to one another of the sample tray, disposable applicator card, test vehicle, and all components of the device itself.

16 Claims, 7 Drawing Figures

FLUID DISPENSING DEVICE

BACKGROUND OF THE INVENTION

1. Field of the Invention

The present invention relates to fluid dispensing devices but in particular to a device for first accepting discrete quantities of one or more test fluids and thereafter dispensing predetermined quantities of such fluids to a test vehicle for diagnostic purposes.

2. Description of the Prior Art

Heretofore dispensers of fluids for test or diagnostic purposes have been complicated syringe devices or multiple applicator devices which use surface tension or capillary action for loading and dispensing fluids. Such devices have been costly, difficult to operate, required excessive cleaning, were susceptible to accidental contamination, and the like. Further, certain of such prior art dispensers did not permit reliable dispensing of predetermined quantities of test fluids thereby affecting the application of such fluids to the test vehicle as well as the results of the test. In addition, numerous problems existed with such prior art dispensers including physical difficulty of filling individual fluid dispensers, the time-consuming nature of such filling, high probability of contaminating adjoining dispensers, and the like. Further, dispensing a precise volume, such as one microliter, a sample by means of a hand held device has been very difficult. Certain of such prior art dispensers were of such construction that test fluids would tend to collect about the dispensing ends whereby the predetermined quantity of test fluid would be affected. Further, such excess fluid would tend to affect the dispensing of the fluid or the application thereof to a test medium. Prior art methods and dispensing devices in general have not been conducive to high speed reliable laboratory testing.

SUMMARY OF THE INVENTION

The objects of this invention are to provide a fluid dispensing device which is simple, economical, easy to use, reliable, provides a fast manner of filling multiple fluid dispensers, impedes contamination between various test specimens, and overcomes the heretofore noted disadvantages.

Broadly, according to the present invention, a vastly improved device for dispensing one or more predetermined quantities of fluids is provided. The fluid dispensing device includes a base plate and support means associated with the base plate suitable for accommodating a disposable applicator card having at least one compressible tube adhered to a backing. Means are provided for filling each of the compressible tubes with a quantity of test fluid and dispensing a predetermined quantity of the test fluid from each compressible tube to a test vehicle. Such means may be a roller disposed so as to have rolling compressible contact with each compressible tube whereby the roller causes a quantity of test fluid to be drawn into each compressible tube through peristaltic-like action. Means such as a sample tray having distinct isolated test fluid reservoirs corresponding in number to the compressible tubes used in any test, is provided as a source of test fluids. Means are also provided for positioning the support means on the base plate so as to provide proper alignment between the compressible tubes and a test vehicle, such as an agarose gel plate, while the predetermined quantity of test fluid or fluids is dispensed thereto. A spring means is associated with the roller so as to maintain the roller in pressure contact with the compressible tubes. The travel of the roller in contact with the compressible tubes is limited in both directions with the limits being adjustable, thereby determining the amount of test fluid drawn into the compressible tubes and predetermining the quantity of test fluid dispensed therefrom. Means are also provided for aligning the disposable applicator card when it is disposed within the support means. The support means may have a ribbed surface and the applicator card would then be disposed adjacent such ribbed surface so that each compressible tube is aligned in a parallel cooperative manner with a corresponding rib. Accordingly, each such rib provides support for a corresponding compressible tube when each such tube is subjected to the rolling action of the roller.

Additional objects, features, and advantages of the present invention will become apparent to those skilled in the art from the following detailed description and the attached drawing on which, by way of example, only the preferred embodiments of this invention are illustrated.

DETAILED DESCRIPTION

It is to be noted that the drawings are illustrative and symbolic of the invention, and there is no intention to indicate scale or relative proportions of the elements shown therein.

Figure 1:
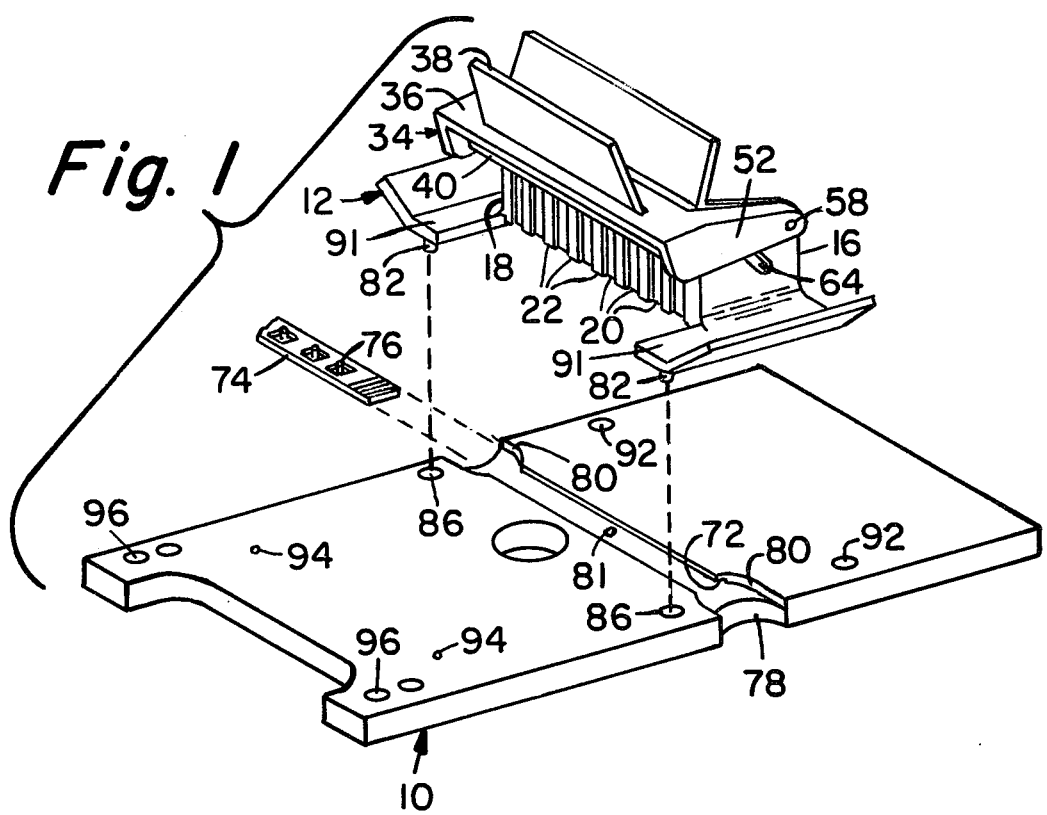
FIG. 1 is an oblique, partly exploded view of the base plate, sample tray, and applicator card holder of the present invention.
Figure 2:
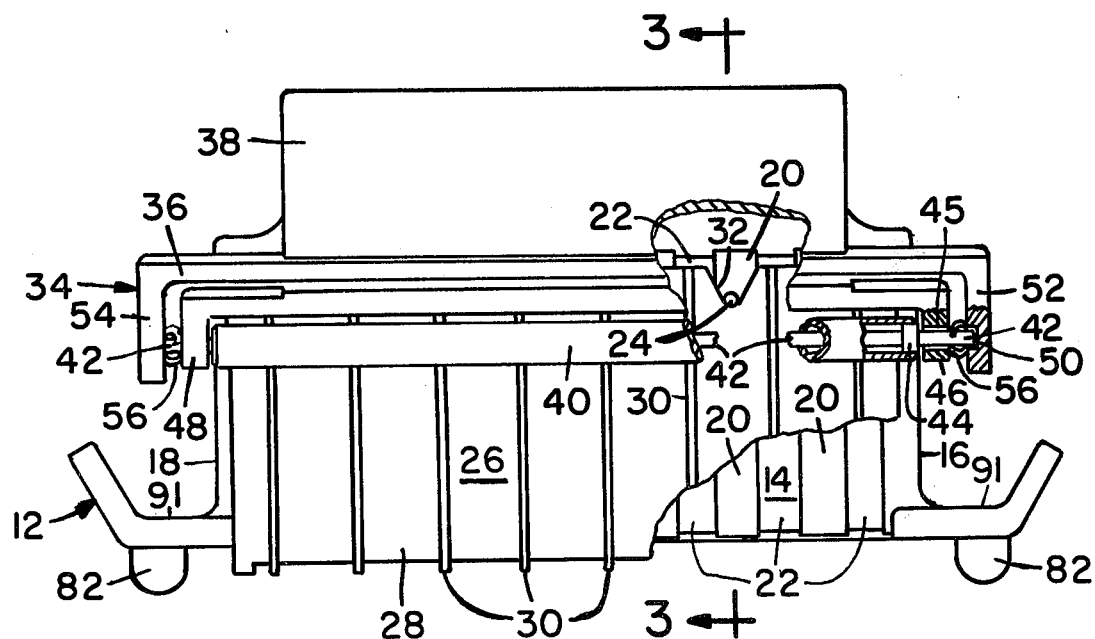
FIG. 2 is a front elevation of an applicator card holder with a disposable applicator card in place.
Figure 3:
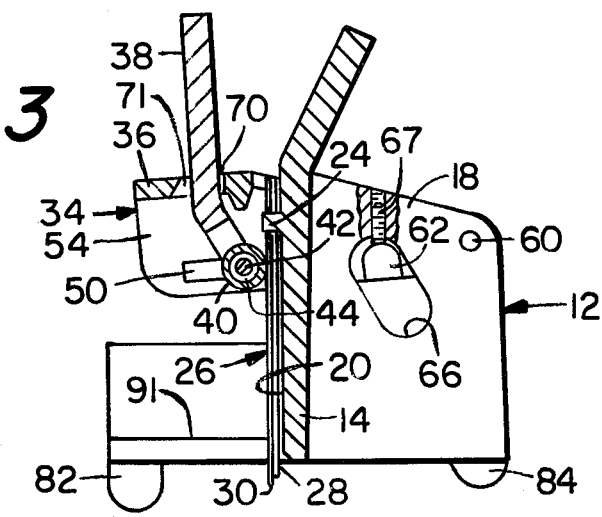
FIG. 3 is a cross-sectional view of the applicator card holder of FIG. 2 taken along lines 3—3 thereof.
Figure 4:
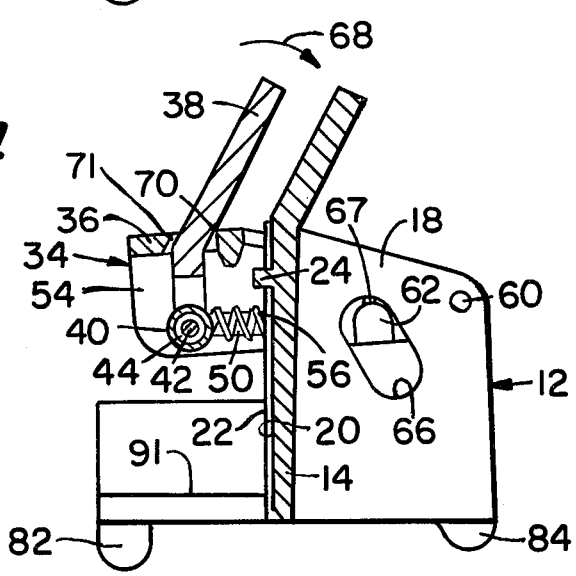
FIG. 4 is a cross-sectional view of the applicator card holder of FIG. 2 in condition to accept a disposable applicator card.

Referring to FIG. 1, there is shown in a partially exploded view a base plate 10 and a support means or disposable applicator card holder 12. Additional details of support means or disposable applicator card holder 12 are shown in FIGS. 2, 3, and 4, and these figures will also be referred to in the following description.

Applicator card holder 12 includes an applicator card aligning and backing member 14 disposed between a pair of end plates 16 and 18. Aligning and backing member 14 may have a plurality of grooves 20 formed in the face thereof, each of said grooves being separated by raised portions or ribs 22. In at least two grooves 20 in backing member 14 a pair of aligning pins 24 are disposed. As will be understood, the face of backing member 14 may be flat without raised portions or ribs 22 if desired.

A disposable applicator card 26 including an absorbent backing 28 to which a plurality of compressible tubes 30 are affixed is positionable adjacent backing member 14 and aligned by means of aligning pins 24 so that compressible tubes 30 are disposed parallel to and in front of raised portions or ribs 22 of the backing member. Aligning pins 24 are eccentrically located within grooves 20 so that an applicator card having corresponding notches 32 formed in one edge thereof can be disposed and positioned adjacent backing member 14 so that notches 32 accommodate aligning pins 24 whereby disposable applicator card 26 can be reproducably positioned within card holder 12. The aligning pins 24 and corresponding notches 32 are eccentrically located so that applicator card 26 cannot be placed in card holder 12 backwards. An example of applicator card 26 is described in U.S. patent application Ser. No. 561,266 by T. O. Lanier and E. F. Martha entitled "Applicator Card" filed concurrently herewith, which application is expressly incorporated herein by reference.

Support means or card holder 12 further embodies a roller assembly 34 including a roller housing 36, roller lever 38, roller 40, roller shaft 42 and roller bearings 44. One roller bearing 44 is mounted in each end of roller 40. Roller shaft 42 is disposed within roller 40 and is accommodated by roller bearings 44. Shaft 42 also extends beyond each end of roller 40 and passes through apertures 45 in lever end supports 46 and 48, and is slidably retained by slide grooves 50 formed in end support members 52 and 54. Lever end supports 46 and 48 are mounted within end support members 52 and 54, respectively, by means of roller shaft 42 being fitted in slide grooves 50. Such a roller mounting permits a rolling and tube compressing engagement of roller 40 with compressible tubes 30. Roller 40 is maintained in a compressible contact with compressible tubes 30 by means of tension springs 56 which transmit their forces to roller 40 through roller shaft 42.

Roller housing 36 is pivotally mounted to end plates 16 and 18 by means of pins 58 and 60, respectively. The rotational or pivotal travel of roller housing 36 about pins 58 and 60 is limited by means of protrusions 62 formed on the interior surfaces of end support members 52 and 54. Slots 64 and 66 are formed in end plates 16 and 18, respectively, to accommodate protrusions 62. As illustrated in FIG. 3, set screws 67 are disposed in end plates 16 and 18 and protrude into slots 64 and 66 to permit adjustment and to limit the pivotal travel of roller housing 36.

The operation of the fluid dispensing device of the present invention is as follows. An applicator card 26 is first placed in card holder 12 by displacing roller 40 from contact with raised portions 22 of aligning and backing member 14. This is accomplished by applying a force to roller lever 38 in the direction of arrow 68 as illustrated in FIG. 4. By applying a force on roller lever 38 as illustrated, the roller level will pivot about surface or edge 70 of lever accommodating aperture 71 in roller housing 36 causing tension springs 56 to be extended and roller 40 to follow roller shaft 42 in slide grooves 50. Applicator card 26 may then be inserted between roller 40 and backing member 14 so that absorbent backing 28 is disposed adjacent to and in contact with raised portions 22, and aligning pins 24 engage the bottom of notches 32 in the upper edge of applicator card 26. With the applicator card so disposed, compressible tubes 30 will be parallel to and directly in front of raised portions 22, backing 28 being disposed intermediate compressible tubes 30 and raised portions 22. Raised portions 22 will thereby support the tubes and absorbent backing while the tubes are filled and emptied. After disposable applicator card 26 is in place, the force applied to roller lever 38 can be released so that the roller can contact compressible tubes 30 as illustrated in FIG. 3, whereby applicator card 26 will be in place and ready for the next step of the procedure.

Referring again to FIG. 1, a channel 72 is provided in base plate 10 to accommodate a simple tray 74 having one or more test specimen reservoirs 76. A suitable test specimen reservoir or sample tray is described in U.S. patent application Ser. No. 561,265 by T. O. Lanier entitled "Sample Tray," filed concurrently herewith, which application is expressly incorporated herein by reference. Briefly, such a sample tray has a plurality of separate elevated reservoirs 76 affixed to a base plate with each elevated reservoir being surrounded by a distinct catch basin. Base plate 10 is provided with finger notches 78 and 80 at both ends of channel 72 to facilitate sliding sample tray 74 in and out of the base plate. In order that sample tray 74 and in turn elevated test specimen reservoirs 76 are properly aligned within channel 72 so that the positioning of the reservoirs with respect to the compressible tubes 30 of applicator card 26 are proper, a depression 81 is provided in the bottom of channel 72 to accommodate an aligning protrusion, not shown, on the bottom of sample tray 74.

Figure 6:
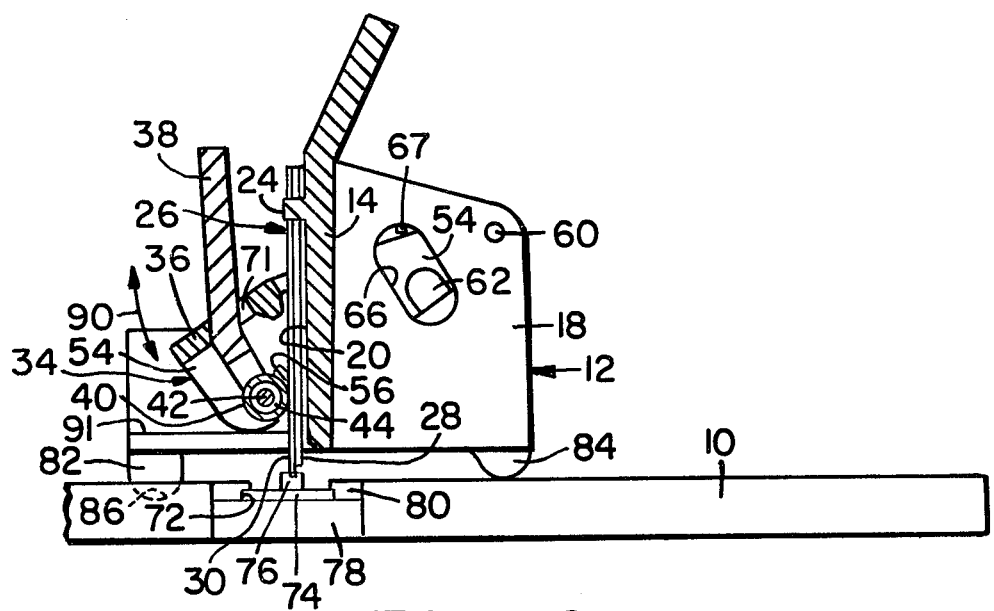
FIG. 6 is a cross-sectional side view of the fluid dispensing device of the present invention in the filling position.

Card holder 12 is provided with a pair of front legs 82 and a pair of rear legs 84. As illustrated in FIGS. 1 and 6, when card holder 12 is in position for filling the compressible tubes 30 of applicator card 26 with quantities of test fluid specimens, card holder 12 is disposed on base plate 10 so that front legs 82 of card holder 12 are fitted into corresponding depressions 86 in base plate 10. As seen in FIG. 6, when front legs 82 are disposed in corresponding depressions 86 rear legs 84 come to rest at the top surface of base plate 10 and compressible tubes 30 of applicator card 26 are aligned with and inserted into elevated reservoirs 76 of sample tray 74.

Figure 5:
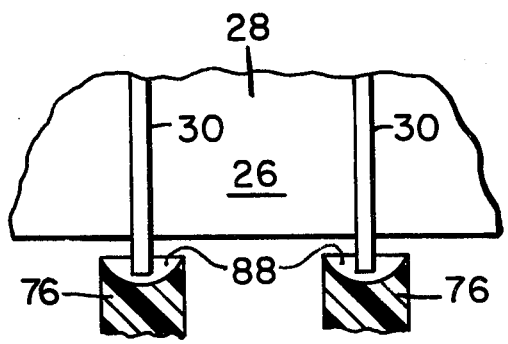
FIG. 5 is a fragmentary view of an applicator card in a tube filling position in cooperation with test fluid reservoirs.

Referring again to FIG. 6, after card holder 12 is suitably disposed on base plate 10 as hereinabove described, with the ends of compressible tubes 30 disposed in fluid containing chambers 88 of elevated reservoirs 76, roller assembly 34 is pivoted about pins 58 and 60 as illustrated by arrow 90. The immersion of compressible tubes 30 in fluid chambers 88 is further illustrated in FIG. 5. As roller assembly 34 is pivoted downwardly with roller 40 in compressible contact with compressible tubes 30, the air in compressible tubes 30 ahead of the roller is expelled therefrom. The pivotal travel of roller assembly 34 is adjustable and controlled by protrusions 62 engaging set screws 67 at the upper end of slots 64 and 66 in end plates 16 and 18, respectively. The air ahead of roller 34 is expelled from tubes 30 until end support members 52 and 54 engage surface 91 of card holder 12 at the lower end of the travel thereof. At this point, compressible tubes 30 are ready to be filled. As roller assembly 34 is permitted to pivot back to its upper position through the force provided by tension springs 56, fluid from each respective elevated reservoir 76 is drawn into its corresponding compressible tube 30 until protrusions 62 engage set screws 67 at the upper ends of slots 64 and 66 in end plates 16 and 18. As can be seen, a controlled amount of travel of roller 40 in contact with compressible tubes 30 is thereby permitted whereby a quantity of fluid is accepted into compressible tubes 30 through peristaltic-like action of roller 40 on compressible tubes 30. In this manner a desired quantity of fluid is taken into the compressible tubes. As will be understood, when compressible tubes 30 are withdrawn from the elevated reservoirs some fluid may adhere thereto between the ends of the tubes and the absorbent backing. Such undesirable excess fluid is readily absorbed by absorbent backing 28 through capillary action leaving the exterior of compressible tubes 30 substantially dry.

Figure 7:
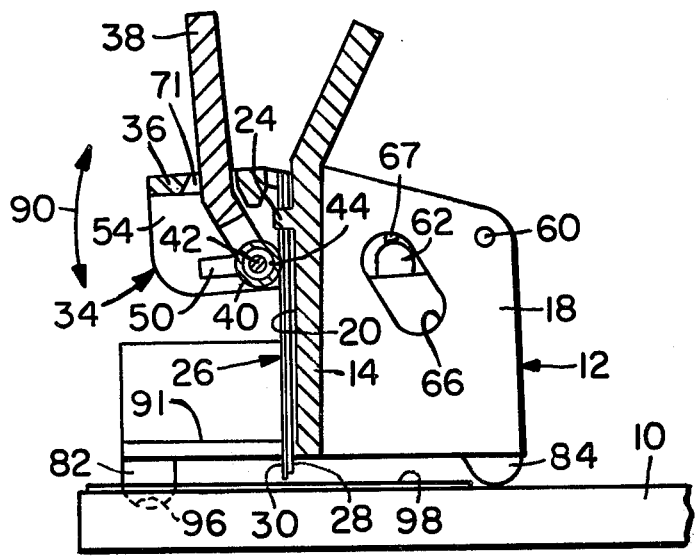
FIG. 7 is a cross-sectional side view of the fluid dispensing device of the present invention in the fluid dispensing position.

After the compressible tubes of applicator card 26 are filled with a sufficient quantity of test fluid, card holder 12 with applicator card 26 maintained in place may be removed from its filling position and disposed over the rear portion of base plate 10 so that front legs 82 engage a second set of depressions 92. This is a holding position which will permit any excess fluid adhered to tubes 30 between the ends thereof and absorbent backing 28 to be absorbed while a suitable test vehicle is positioned over slightly recessed locating pins 94. Card holder 12 with applicator card 26 maintained in place is then disposed over the forward portion of base plate 10 so that front legs 82 engage depressions 96 as illustrated in FIG. 7. By disposing card holder 12 in this manner it is properly aligned to dispense a predetermined quantity of fluid from compressible tubes 30 to some test vehicle. A suitable test vehicle may be one, such for example as, an agarose gel plate 98. Various test vehicles are well known in the art as in an agarose gel plate. With the agarose gel plate 98 properly disposed on the surface of base plate 10, over plate locating pins 94, a predetermined quantity of test fluid is dispensed from each compressible tube 30 to its corresponding test area on the agarose gel plate test vehicle 98. The quantity of the test vehicle is predetermined by the travel of roller 40 as heretofore described. The fluid is dispensed by means of roller 40 compressing compressible tubes 30 thereby forcing the fluid from each tube out ahead of it. The agarose gel plate test vehicle 98 is then processed in a manner well known in the prior art, which processing forms no part of the present invention. The disposable applicator card 26 is then removed from card holder 12 in the reverse manner of its loading and is discarded. Sample tray 74 is removed from base plate 10 and is also discarded.

Although the present invention has been described with respect to specific details of certain embodiments thereof, it is not intended that such details be limitations upon the scope of the invention except insofar as set forth in the following claims.

We claim:

1. A fluid dispensing device comprising
   a base plate,
   support means operatively associated with said base plate suitable for operatively accommodating an applicator card having at least one compressible tube adhered to a backing, and
   means operatively associated with said support means suitable for filling each said compressible tube with a quantity of test fluid and dispensing a predetermined quantity of said test fluid from each said compressible tube to a test vehicle.

2. The fluid dispensing device of claim 1 further comprising a means for providing at least one distinct quantity of test fluid to each said compressible tube.

3. The fluid dispensing device of claim 2 wherein said means for providing is a sample tray disposed on said base plate, said sample tray having at least one test fluid reservoir suitable for containing one discrete quantity of said test fluid.

4. The fluid dispensing device of claim 2 further comprising means for positioning said support means on said base plate so as to provide proper alignment between said compressible tubes and said means for providing at least one quantity of test fluid while said tubes are being filled.

5. The fluid dispensing device of claim 2 further comprising means for positioning said support means on said base plate so as to provide proper alignment between said compressible tubes and said test vehicle while said predetermined quantity of said test fluid is dispensed.

6. The fluid dispensing device of claim 2 wherein said means operatively associated with said support means comprises a roller disposed so as to have rolling compressible contact with each said compressible tube, said roller being suitable for drawing into each said compressible tube a quantity of test fluid through peristaltic-like action.

7. The fluid dispensing device of claim 3 further comprising means for firmly maintaining said sample tray within said base plate.

8. The fluid dispensing device of claim 6 further comprising spring means associated with said roller so as to maintain said roller in pressure contact with said compressible tubes.

9. The fluid dispensing device of claim 6 further comprising means for limiting the travel of said roller in contact with said compressible tubes.

10. The fluid dispensing device of claim 1 further comprising means for aligning said applicator card in cooperation with said support means.

11. The fluid dispensing device of claim 1 further comprising means for aligning said test vehicle on said support means.

12. The fluid dispensing device of claim 1 wherein said support means comprises a ribbed surface, said applicator card being disposable adjacent said ribbed surface so that each said compressible tube is aligned in a parallel cooperative manner with a corresponding rib.

13. The fluid dispensing device of claim 6 further comprising
   means for positioning said support means on said base plate so as to provide proper alignment between said compressible tubes and said means for providing at least one quantity of test fluid while said tubes are being filled,
   means for positioning said support means on said base plate so as to provide proper alignment between said compressible tubes and said test vehicle while said predetermined quantity of test fluid is dispensed,
   spring means associated with said roller so as to maintain said roller in pressure contact with said compressible tubes,
   means for limiting travel of said roller in contact with said compressible tubes, and
   means for aligning said applicator card in cooperation with said support means.

14. The fluid dispensing device of claim 13 wherein said means for providing is a sample tray disposed on said base plate, said sample tray having at least one test fluid reservoir suitable for containing one discrete quantity of said test fluid.

15. The fluid dispensing device of claim 14 further comprising means for firmly maintaining said sample tray within said base plate.

16. The fluid dispensing device of claim 13 wherein said support means comprises a ribbed surface, said applicator card being disposable adjacent said ribbed surface so that each said compressible tube is aligned in a parallel cooperative manner with a corresponding rib.

* * * * *